(12) United States Patent
Fumex et al.

(10) Patent No.: US 9,572,551 B2
(45) Date of Patent: Feb. 21, 2017

(54) BIOPSY TROCAR

(71) Applicants: Laurent Fumex, Madison, CT (US); Thierry Masseglia, La Garde (FR)

(72) Inventors: Laurent Fumex, Madison, CT (US); Thierry Masseglia, La Garde (FR)

(*) Notice: Subject to any disclaimer, the term of this patent is extended or adjusted under 35 U.S.C. 154(b) by 0 days.

(21) Appl. No.: 14/551,435

(22) Filed: Nov. 24, 2014

(65) Prior Publication Data

US 2015/0150541 A1    Jun. 4, 2015

(51) Int. Cl.
| | | |
|---|---|---|
| *A61B 10/02* | (2006.01) | |
| *A61B 17/34* | (2006.01) | |
| *A61B 17/32* | (2006.01) | |
| *A61B 17/3205* | (2006.01) | |

(52) U.S. Cl.
CPC ...... *A61B 10/025* (2013.01); *A61B 17/32053* (2013.01); *A61B 17/3472* (2013.01); *A61B 2010/0208* (2013.01); *A61B 2010/0258* (2013.01); *A61B 2017/320064* (2013.01); *A61B 2017/3458* (2013.01)

(58) Field of Classification Search
CPC ...................... A61B 2010/0258; A61B 10/025
USPC .................................................. 600/564–568
See application file for complete search history.

(56) References Cited

U.S. PATENT DOCUMENTS

| | | | | |
|---|---|---|---|---|
| 4,099,518 A * | 7/1978 | Baylis | ................. | A61B 10/025 30/113.1 |
| 5,257,632 A * | 11/1993 | Turkel | ................. | A61B 10/025 600/567 |
| 6,019,776 A | 2/2000 | Preissman et al. | | |
| 6,086,543 A * | 7/2000 | Anderson | .......... | A61B 10/0233 600/567 |
| 6,110,128 A | 8/2000 | Andelin et al. | | |
| 6,315,737 B1 * | 11/2001 | Skinner | ................. | A61B 10/025 600/566 |
| 7,850,620 B2 | 12/2010 | Miller et al. | | |
| 7,988,643 B2 | 8/2011 | Hoffmann et al. | | |
| 2006/0142779 A1 * | 6/2006 | Arramon | ............ | A61B 17/3421 606/92 |
| 2007/0016100 A1 | 1/2007 | Miller | | |
| 2008/0146964 A1 * | 6/2008 | Hoffmann | ............ | A61B 10/025 600/567 |
| 2008/0300507 A1 * | 12/2008 | Figueredo | .......... | A61B 10/0266 600/567 |
| 2009/0194446 A1 | 8/2009 | Miller et al. | | |
| 2011/0082387 A1 * | 4/2011 | Miller | .................. | A61B 10/025 600/567 |
| 2014/0213931 A1 * | 7/2014 | Lee | .................... | A61B 10/0233 600/567 |

OTHER PUBLICATIONS

International Search Report dated 2014.

* cited by examiner

*Primary Examiner* — Michael C Stout
(74) *Attorney, Agent, or Firm* — Sofer & Haroun, LLP

(57) ABSTRACT

A biopsy trocar (1) is provided for performing bone marrow biopsies. The trocar comprises a biopsy needle (2) having a cannula (4), and a mandrel (3) having a shaft (6), the shaft (6) being suitable for sliding in the biopsy needle (2). The cannula (4) has, at its distal end, at least one internal rib (12, 21) forming a helix portion on the internal wall of the cannula (4), and the shaft (6) has a helical groove (16, 26) that is able to cooperate with the internal rib (12, 21), the internal rib (12, 21) being suitable for retaining a sample of marrow in the needle (2).

13 Claims, 4 Drawing Sheets

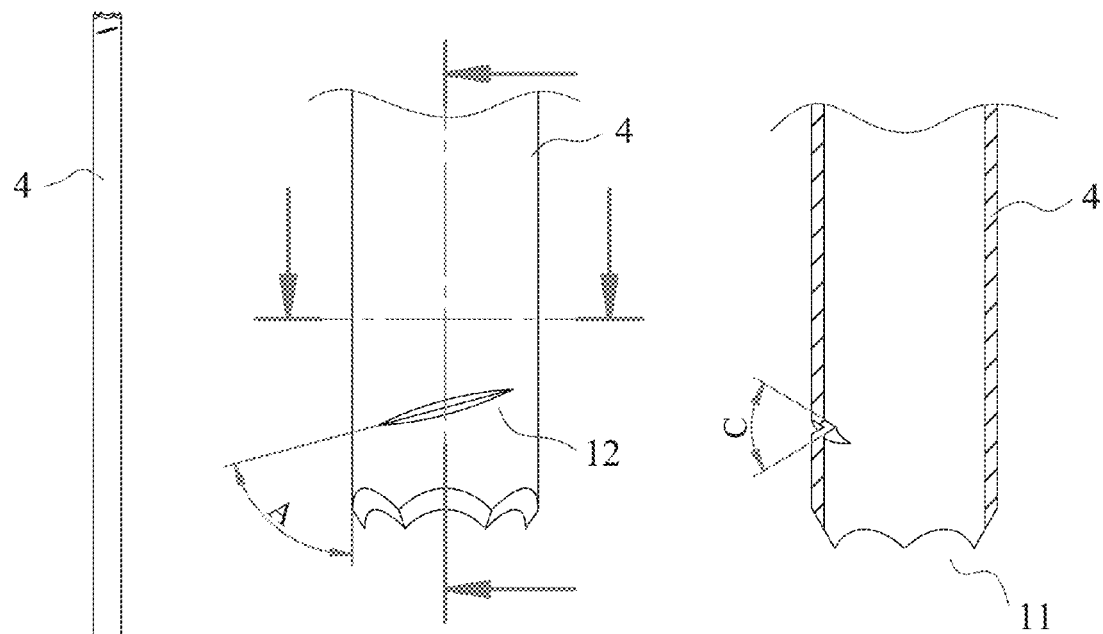
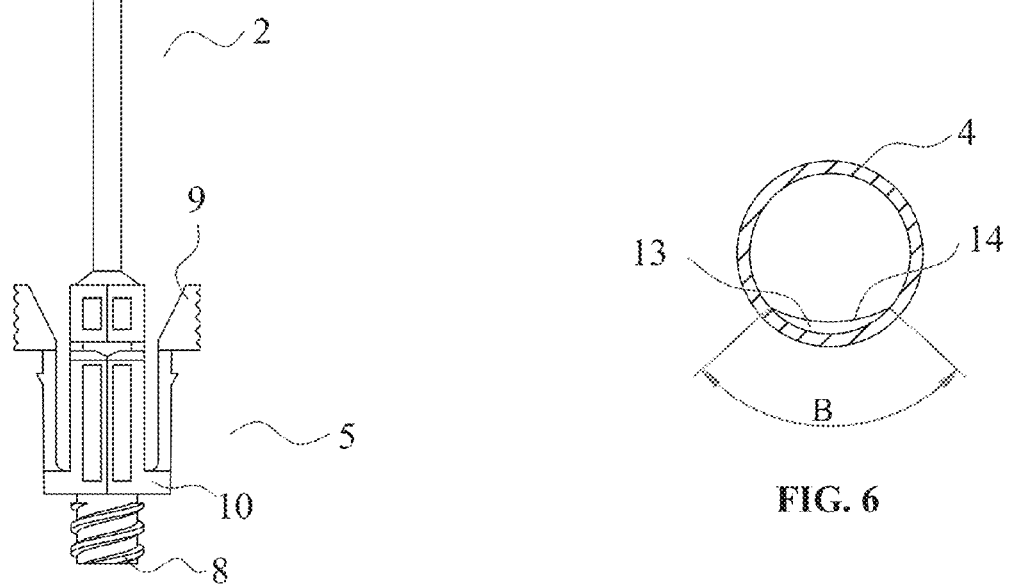
FIG. 3  FIG. 4  FIG. 5  FIG. 6

BIOPSY TROCAR

RELATED APPLICATION

This application claims the benefit of priority from French Patent Application No. 13 62009, filed on Dec. 3, 2013, the entirety of which is incorporated by reference.

BACKGROUND

Field of the Invention

The present invention relates to a trocar for bone marrow biopsy, and to a device for bone marrow biopsy that connects a trocar to a motorized rotational drive means.

Description of Related Art

The techniques for performing bone marrow biopsies are the fine-needle biopsies by puncture and aspiration of the marrow (myelogram) and the osteo-medullary biopsies for collecting samples of the marrow and the medullary stroma, the choice being dependent on the result sought by the practitioner (cytology or histology).

Biopsy by aspiration can be performed using a fine needle with a 15-16 gauge, for example. By contrast, if the desired result is of a histological nature, use will preferably be made of the osteo-medullary trocars with a greater diameter (13 gauge for example), thereby allowing a larger sample to be collected.

Traditionally, bone marrow biopsies of the osteo-medullary type are performed especially in the crest of the iliac bone where there is fine cortical bone substance. To perform these biopsies, the procedures presently carried out are either manual or motorized. The manual procedures have certain disadvantages, the main ones being associated with the penetration into the cortical bone and with the recovery of the sample. Most of the needles used manually have simple mandrels with a trocar tip that is not especially sharp, thus forcing the practitioner to exert considerable pressure during the penetration into the bone. The procedure may therefore prove particularly awkward and may cause pain and discomfort for the patient. Once the cortical bone substance has been penetrated and the mandrel withdrawn, the needle is driven into the bone by several millimeters (10 to 30 mm) in order to recover a sample of marrow and medullary stroma. Before the withdrawal of the needle, and in order to ensure that the tissue sample is maintained in the needle, it is recommended to tilt the needle to and fro slightly and rotate it. This manoeuvre makes it possible to cut the specimen and contributes to the successful recovery of the sample. However, it is particularly painful for the patient.

The motorized procedures significantly attenuate the difficulties of penetration and sampling and are less painful for the patient; they also make it possible to reduce the length of time it takes the practitioner to perform the procedure.

U.S. Pat. No. 6,019,776 discloses an access trocar used in particular in vertebroplasty for injection of materials, comprising a cannula and a stylet, the stylet being guided in the cannula. The cannula and the stylet have threads which allow the cannula to be positioned on the stylet and to advance to a predetermined position. The stylet also has a bone-drilling thread at its distal end. The thread of the cannula is not suitable for retaining a marrow sample since it is too far from the distal end of the cannula.

U.S. Pat. No. 6,086,543 describes a biopsy trocar for soft tissues. The cannula of the trocar has, at its distal end, a thread for retaining the tissues during the withdrawal of the cannula.

U.S. Pat. No. 7,988,643 describes a biopsy trocar for manual use which, on the distal end of the needle, has an internal thread and external thread, and also a conical part. This needle is connected to a handle. This device has the major disadvantage of having an external thread which, on account of the bone density, will be very difficult to remove without having to unscrew it, which will not allow the marrow sample to be withdrawn correctly.

U.S. Pat. No. 6,110,128 describes a biopsy trocar for manual use, characterized in that the needle has internal ribs inclined towards the rear. This device will not permit bone marrow biopsies of good quality, since the ribs will oppose the penetration of the marrow into the needle. The reason is that, since the trocar is used manually, the speed of rotation is not fast enough to drive the marrow into the needle. In addition, the formation of ribs as described in the patent is technically complicated and very costly.

U.S. Pat. No. 7,850,620 describes a trocar for motorized use, having a needle with a helical thread portion that is welded inside the distal end, making it easier for the marrow to enter the needle during the biopsy, and a mandrel whose distal end is ground to a pyramidal point. This trocar has several disadvantages. Since the external diameter of the mandrel is less than the internal diameter of the thread crest, there is quite significant play between the external diameter of the mandrel and the internal diameter of the needle. This play may cause accidental attachment and therefore tearing of the soft tissue parts during the introduction of the trocar, but also clogging with bone debris during the perforation of the cortical bone. This clogging may cause difficulties when removing the mandrel from the needle, since the mandrel remains affixed to the internal wall of the needle. It may also cause accidental entry of debris between the mandrel and the internal wall of the needle, thus creating a coating of the internal wall, of which the thickness may be equal to the height of the crest of the welded thread. The efficacy of the system for recovering the specimen, and therefore of the welded thread, is then compromised since the welded thread is in fact embedded within the thickness of the coating and becomes ineffective for the following step of performing the biopsy proper. Finally, the formation of such a thread by welding is technically difficult and particularly costly. Of course, the difficulty increases significantly as the size of the needles decreases.

These trocars make it possible to perform bone marrow biopsies, but, in the case of the manual devices, with longer and more painful operating techniques and, in the case of the motorized device, with risks of failure due to clogging.

OBJECTS AND SUMMARY

The object of the present invention is to make available a trocar which is intended for performing bone marrow biopsies and which makes it possible to perform safe, reliable and rapid biopsies irrespective of the diameter of the needle, and at a reasonable cost.

The biopsy trocar according to the present invention comprises a biopsy needle having a cannula, and a mandrel having a shaft, the shaft being suitable for sliding in the biopsy needle. The cannula has, at its distal end, at least one internal rib forming a helix portion on the internal wall of the cannula, and the shaft has at least one helical groove cooperating with the internal rib. The internal rib is suitable for retaining a sample of marrow in the needle.

Advantageously, the axis of the helix portion of the internal rib is off-centred with respect to the axis of the cannula. Thus, the width or the thickness of the internal rib, in the plane of the cross section of the cannula, varies from 0 at its ends to several tenths of the internal diameter of the cannula at the centre of the internal rib. These features distinguish the internal rib from an internal thread.

By virtue of the rib, the marrow sample is retained in the needle when the latter is withdrawn from the patient. Moreover, the small extent (or length) of the internal rib on the internal diameter of the cannula does not prevent the marrow from entering the needle and instead facilitates this, while at the same time exerting minimal retention force for easy ejection of the marrow sample without damage.

Advantageously, the cannula has only a single internal rib. In this way, the penetration of the marrow into the cannula is made considerably easier.

According to embodiments, the width of the internal rib varies from 0 at its ends to 20% of the value of the internal diameter of the cannula at the centre.

Advantageously, the inclination of the internal rib with respect to the axis of the cannula and the inclination of the helical groove are identical.

According to embodiments, the inclination of the internal rib with respect to the axis of the cannula has a value of between 65° and 80°.

Preferably, the inclination of the internal rib with respect to the axis of the cannula is 75°.

According to one feature of the invention, the internal rib extends on the internal wall of the cannula at an angle of between 30° and 180°.

Advantageously, the internal rib has a cross section of angular shape with an angle of between 10° and 120°.

Preferably, the angle of the cross section is 60°.

Preferably, the internal rib is a helix portion whose pitch is to the right, and the helical groove has a right-hand pitch.

Advantageously, the mandrel screws into the needle. The assembly formed by the needle and the mandrel is suitable for being mounted in an automatic rotational drive means.

According to another aspect, the present invention also relates to a biopsy device for performing bone marrow biopsies, comprising a trocar according to the above-described embodiments and an automatic rotational drive means, to which the trocar is rigidly connected. This automatic rotational drive means can be a drill, for example a drill providing 300 to 400 rpm.

By virtue of the internal rib, the sample of the marrow is driven more easily into the cannula, the device belonging to that of an endless screw by reason of the combination of the inclination of the internal rib and of the speed of rotation of the drill. Since the speed of penetration of the device into the bone or into the marrow is always less than the theoretical speed of penetration of the internal rib, as a result of its theoretical pitch, the ascent of the sample into the needle is guaranteed.

The presence of an internal rib and of a helical groove which engage in each other also makes it possible to more closely adjust the mandrel and the needle and to thus reduce the risks of attachment of soft tissue parts, and then of clogging by bone debris during penetration into the cortical bone. Once the mandrel has been withdrawn, the needle is emptied of all debris and the one or more ribs are ready to play their role in full.

The cannula of the biopsy needle can be adhesively bonded or overmoulded in a body and the shaft of the mandrel can be adhesively bonded or overmoulded in a stopper. The cannula has, at its distal end, a faceted grinding currently used for this type of biopsy. The shaft is ground at its distal end in such a way as to drill the bone. The tip can be triangular, lanceolate or a bore bit.

Advantageously, the cannula and the shaft are made of biocompatible materials, for example of the stainless steel type. The body and the stopper are made of plastic for medical uses.

The advantages of the present invention will become clearer from the following explanation. The practitioner takes hold of the mandrel, slides it into the biopsy needle and rigidly connects them by screwing the mandrel into the biopsy needle until the stopper is blocked against the body. This assembly forms the trocar. The practitioner clips the trocar into the specially adapted endpiece of a sterile drill and then passes it through the soft tissues until it comes into contact with bone. At this moment he activates the drill and drills the cortical bone. Once the cortical bone is perforated, he unclips the trocar from the endpiece of the drill, unscrews the mandrel and withdraws it from the biopsy needle fixed in the bone. He clips the drill back on to the biopsy needle, then collects a sample of the bone marrow by actuating and pushing the drill. When the desired depth is reached, and having let the drill turn for a few seconds at the same position in order to section the marrow, he withdraws the drill with the needle while keeping the drill actuated. Having unclipped the drill, the practitioner ejects the sample from the biopsy needle by pushing it through the distal end of the needle by means of an ejector.

BRIEF DESCRIPTION OF THE DRAWINGS

Other features and advantages of the present invention will become clear from the following description of preferred embodiments of the invention and by reference to the attached drawings, in which:

FIG. 3 shows a view of a biopsy needle of the trocar according to the invention;

FIGS. 4 to 6 show views illustrating the distal end of a cannula of the trocar according to the invention;

DETAILED DESCRIPTION

Figure 1:
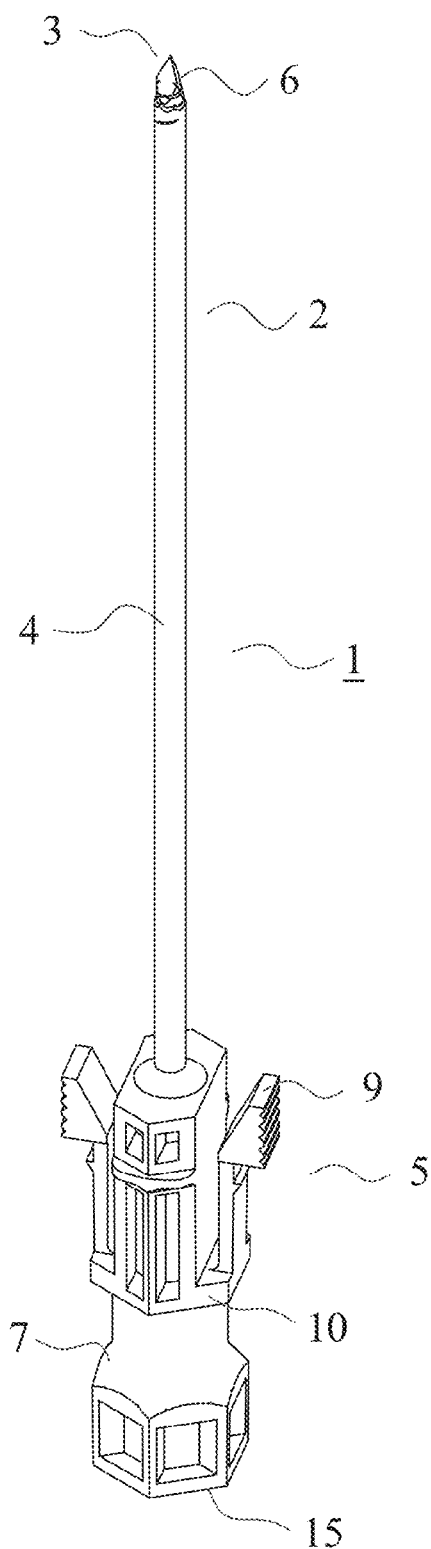
FIG. 1 shows a perspective view of a trocar according to the invention.
Figure 2:
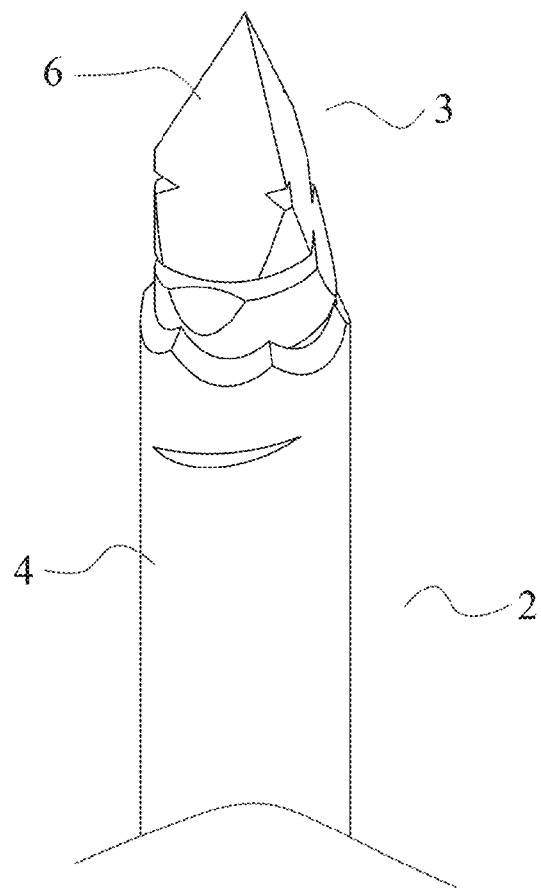
FIG. 2 shows a perspective view of the distal end of the trocar according to the invention.

The trocar 1 according to the present invention, shown in FIG. 1, is composed of a biopsy needle 2 and of a mandrel 3. The biopsy needle 2 is formed by a cannula 4 lodged in a body 5. The mandrel 3 is formed by a shaft 6 lodged in a stopper 7. FIG. 2 shows the distal end of the trocar 1 in more detail.

FIG. 3 shows the biopsy needle 2, of which the body 5 is composed of a Luer connector 8 and a snap-fit system 9. The shape 10 of the body 5 is hexagonal and cooperates, for example, with a hexagonal cavity of an endpiece of a drill. The snap-fit system 9 has two flexible parts that snap into recesses in the endpiece of the drill machine, allowing the trocar 1 to be supported and driven in rotation. The Luer connector 8 makes it possible, for example, to connect a syringe to the biopsy needle 2 in order to aspirate marrow, if this is necessary during a surgical procedure.

FIGS. 4 to 6 show the distal part of the cannula 4. FIGS. 5 and 6 show sections along the lines indicated in FIG. 4. A bevelled grinding 11 formed at the distal end of the cannula 4 is traditionally used for bone marrow biopsy. The cannula 4 additionally has an internal rib 12. The internal rib 12 is oriented in such a way as to form a helix portion on the internal wall of the cannula 4. The pitch of the helix is a right-hand pitch, since the direction of manual or automatic rotation of the trocar during its operation is to the right. The helix portion is inclined at an angle A with respect to the axis of the cannula 4. According to the embodiments, the value of the angle A is between 65° and 80° and is preferably 75°. The internal rib 12 is formed, for example, approximately 2 mm from the distal end of the cannula 4. As is illustrated in FIG. 6, the internal rib 12 forms an arc of a circle 13 having an angle B of between 30° and 180°. Preferably, the angle B of the arc of a circle 13 is approximately 120°.

Preferably, the internal rib 12 has a cross section of angular shape, as is shown for example in FIG. 5. The angle C has a value of between 10° and 120°. Preferably, the value of the angle C is 60°.

The internal rib 12 is preferably formed by stamping the external wall of the cannula 4, as is illustrated in FIGS. 4 and 5. This stamping is carried out by means of a cylindrical die with at least one helical groove corresponding to the shape to be obtained, which is lodged in the cannula 4, and at least one punch, whose distal end corresponds to the shape to be obtained, passing through a metal block in which the cannula 4 is lodged with the die in a bore whose diameter is slightly greater than the external diameter of the cannula 4, thus making it possible to obtain the one or more ribs without deformation and perforation of the external diameter of the cannula 4. This permits quick and simple production of the internal rib 12 by avoiding welding work in the cannula 4, the latter having an internal diameter of only a few mm. In addition, the stamping can be carried out on all types of existing trocars, thereby making them more effective.

Referring to FIG. 6, the value of the diameter of the apex 14 of the helix of the internal rib 12 is greater than the value of the internal diameter of the cannula 4. The axis of the helix portion of the apex 14 of the internal rib 12 is off-centred with respect to the axis of the cannula. Thus, the width or the thickness of the internal rib 12, in the plane of the cross section of the cannula 4, varies from 0 mm at its ends to several tenths with respect to the internal diameter of the cannula 4 at the centre of the internal rib 12. For example, the maximum width of the internal rib 12 at the centre can be between 0.1 mm and 0.5 mm for an internal diameter of the cannula 4 of 2.5 mm, which corresponds to a maximum width of approximately 20% of the value of the internal diameter of the cannula 4.

Of course, the representation of the shape of the apex 14 of the rib 12 is not limited to just a cylindrical shape, and instead it can be of a plane shape or a combination of plane shapes and/or a combination of plane and cylindrical shapes. In all cases, the parts forming the apex 14 of the rib 12 can be regarded as helix portions of variable diameter. The axis of at least one of the parts of the apex 14 is thus off-centred with respect to the axis of the cannula 4.

Figure 7:
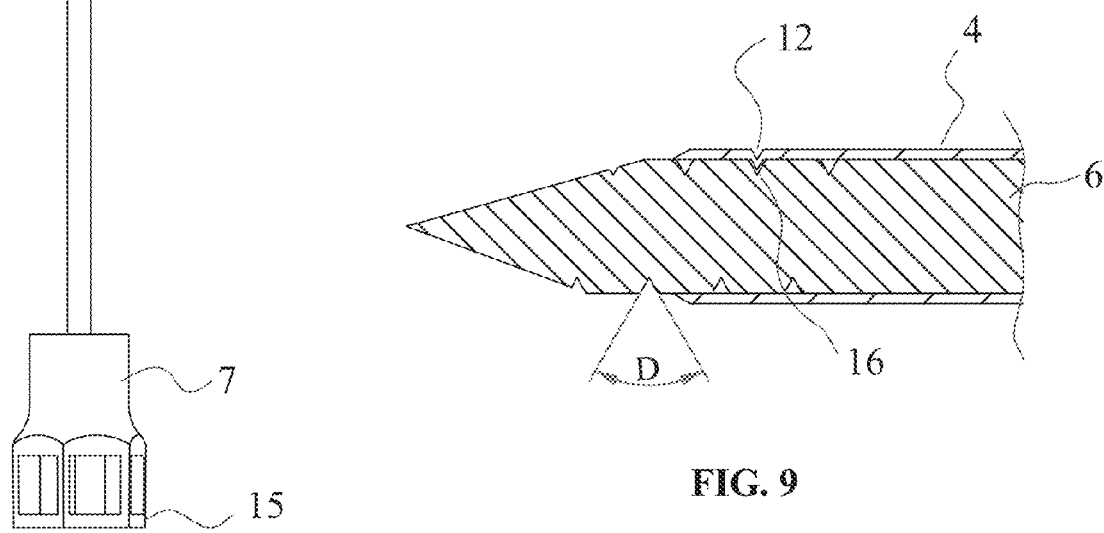
FIG. 7 shows a view of a mandrel of the trocar according to the invention.

FIG. 7 shows the mandrel 3, of which the stopper 7 has a hexagonal shape 15 cooperating with the cavity of hexagonal shape of the endpiece of a drill, making it possible to maintain the mandrel 3 in position with respect to the biopsy needle 2 during the rotation of the drill.

Figure 8:
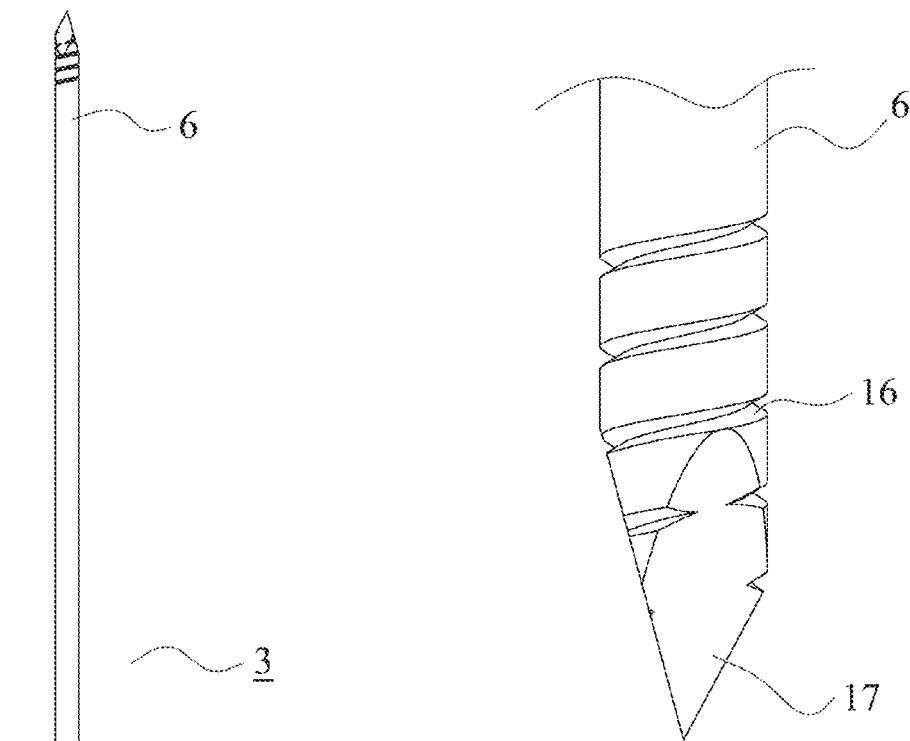
FIG. 8 shows a view of the end of a shaft of the trocar according to the invention.

FIG. 8 shows the distal part of the shaft 6 comprising a helical groove 16, of which the angulation cooperates with the angle A of the internal rib 12 of the cannula 4. The cross section of the helical groove 16 has an angular shape. The distal end of the shaft 6 has a traditionally ground cutting part 17 that permits drilling of the iliac cortical bone.

Figure 9:
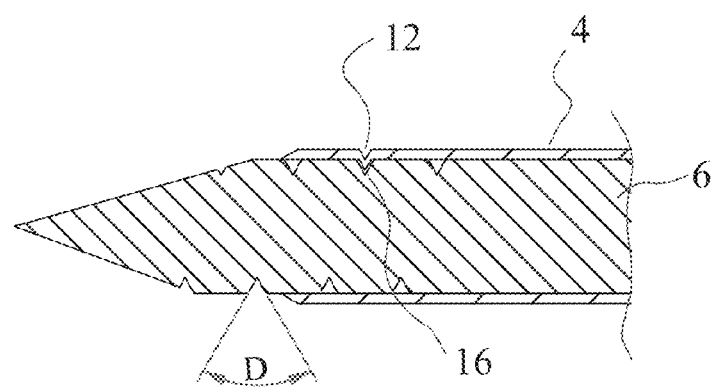
FIG. 9 shows a sectional view of the distal end of the trocar according to the invention.

FIG. 9 shows a longitudinal sectional view of the distal end of the trocar 1 comprising the cannula 4 and the shaft 6. The play existing between the internal rib 12 and the helical groove 16 can be seen. The angle D of the helical groove 16 is greater than or equal to the angle C of the internal rib 12 (see FIG. 5), and the depth of the helical groove 16 is greater than the width or the maximum thickness of the internal rib 12.

Figure 10:
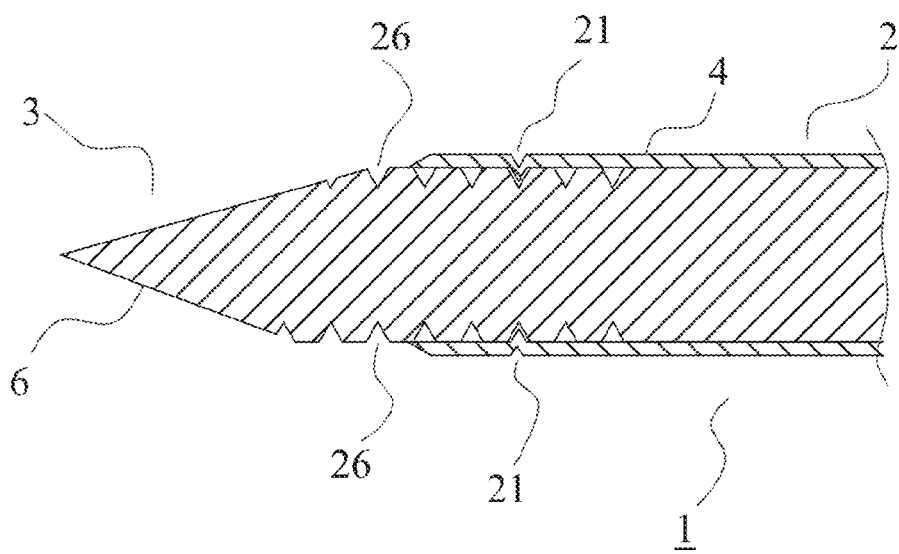
FIG. 10 shows a sectional view of the distal end of a variant of the trocar according to the invention.

FIG. 10 shows a sectional view of the distal end of the trocar 1 according to a variant. The trocar 1 comprises a biopsy needle 2, of which the cannula 4 has two diametrically opposite internal ribs 21, and a mandrel 3, of which the shaft 6 has two helical grooves 26 cooperating with the internal ribs 21 of the cannula 4.

Figure 11:
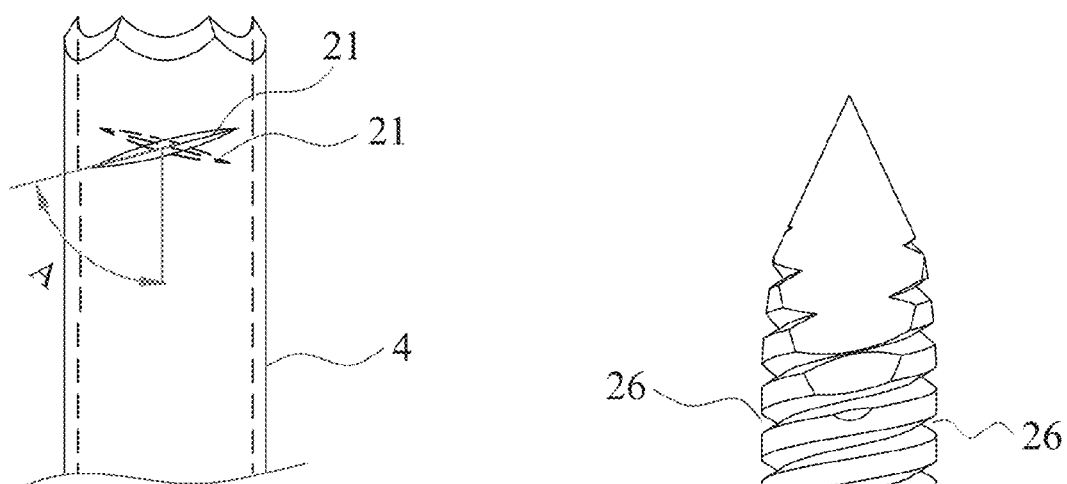
FIGS. 11 and 12 show views of the distal end of a variant of the cannula according to the invention.
Figure 12:

FIGS. 11 and 12 show views of the distal part of the cannula 4 having, at its distal end, two diametrically opposite internal ribs 21. The internal ribs 21 can be formed approximately 2 mm from the distal end of the cannula 4. They are oriented in such a way as to form two helix portions, which have a right-hand pitch and are inclined with respect to the axis of the cannula 4 by the same angle A.

Figure 13:
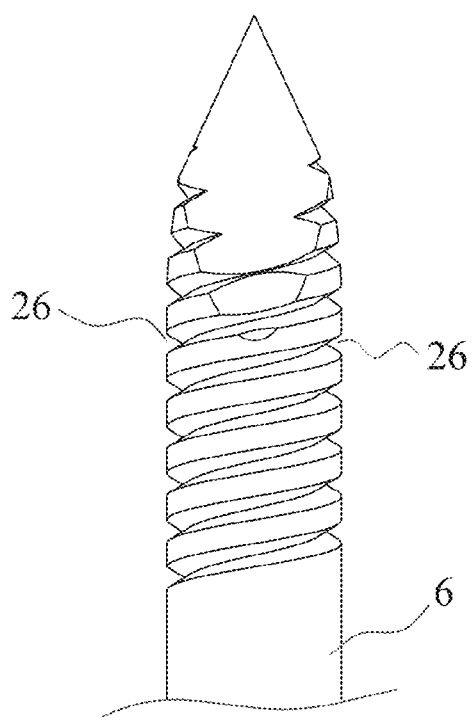
FIG. 13 shows a view of the distal end of a variant of the shaft according to the invention.

FIG. 13 shows the distal part of the shaft 6 comprising two helical grooves 26, of which the angulations cooperate with the angle A of the internal ribs 21.

The biopsy device according to the present invention, intended for performing bone marrow biopsies, comprises a trocar 1 according to one of the above-described embodiments and a drill (not shown) on which the trocar 1 is mounted. In one example, with the drill having a speed of rotation of 6 revolutions per second, for a bone marrow depth to be penetrated of 30 mm, and with the average sampling time being 4 seconds, the average speed of penetration of the cannula is 7.5 mm/sec. With the theoretical pitch of the helix of the internal rib 12 being 1.39 mm, the theoretical speed of penetration of the cannula 4 is 1.39 mm×6 revolutions/sec=8.34 mm/sec. The difference between the average speed of penetration and the theoretical speed of penetration of the cannula 4 thus generates the effect of an endless screw, by means of which the bone marrow is driven into the cannula 4.

The invention claimed is:

1. Biopsy trocar for performing bone marrow biopsies, comprising:
    a biopsy needle having a cannula; and
    a mandrel having a shaft, the shaft being suitable for sliding in the biopsy needle, wherein:
    the cannula has, at its distal end, at least one internal rib forming a helix portion on the internal wall of the cannula,
    the axis of the helix portion of at least a part of the apex of the internal rib is off-centred with respect to the axis of the cannula,
    the diameter of the apex of the helix of the internal rib is greater than the internal diameter of the cannula,
    the shaft has at least one helical groove cooperating with the internal rib,
    the internal rib being suitable for retaining a sample of marrow in the needle.

2. Trocar according to claim 1, in which the width of the internal rib varies from 0 at its ends to several tenths of the value of the internal diameter of the cannula at the centre.

3. Trocar according to claim 1, in which the inclination of the internal rib with respect to the axis of the cannula and the inclination of the helical groove are identical.

4. Trocar according to claim 1, in which the inclination of the internal rib with respect to the axis of the cannula has a value of between 65° and 80°.

5. Trocar according to claim 1, in which the inclination of the internal rib with respect to the axis of the cannula is 75°.

6. Trocar according to claim 1, in which the internal rib extends on the internal wall of the cannula at an angle of between 30° and 180°.

7. Trocar according to claim 1, in which the internal rib has a cross section of angular shape with an angle of between 10° and 120°.

8. Trocar according to claim 7, in which the angle of the cross section is 60°.

9. Trocar according to claim 1, in which the internal rib is a helix portion whose pitch is to the right, and the helical groove has a right-hand pitch.

10. Trocar according to claim 1, in which the mandrel screws into the needle.

11. Trocar according to claim 1, in which combined elements of said assembly, including said needle and said mandrel, are mounted in an automatic rotational drive means.

12. Biopsy device for performing bone marrow biopsies, comprising:
    a trocar according to claim 1; and
    an automatic rotational drive means, to which the trocar is rigidly connected.

13. Trocar according to claim 1, wherein the internal rib is formed by stamping the external wall of the cannula.

* * * * *

UNITED STATES PATENT AND TRADEMARK OFFICE
CERTIFICATE OF CORRECTION

PATENT NO. : 9,572,551 B2  
APPLICATION NO. : 14/551435  
DATED : February 21, 2017  
INVENTOR(S) : Fumex et al.

Page 1 of 1

It is certified that error appears in the above-identified patent and that said Letters Patent is hereby corrected as shown below:

On the Title Page

At Item (30), please insert, Foreign Application Priority Data:  
--France 13 62009, filed December 3, 2013--.

Signed and Sealed this  
Twenty-seventh Day of June, 2017

Joseph Matal  
*Performing the Functions and Duties of the*  
*Under Secretary of Commerce for Intellectual Property and*  
*Director of the United States Patent and Trademark Office*